(12) United States Patent
Lee et al.

(10) Patent No.: US 8,786,859 B2
(45) Date of Patent: Jul. 22, 2014

(54) HIGH RESOLUTION SURFACE PLASMON RESONANCE SENSOR AND SENSOR SYSTEM THEREOF

(75) Inventors: Kyeong Seok Lee, Seoul (KR); Won Mok Kim, Seoul (KR); Taek Sung Lee, Seoul (KR); Byung Ki Cheong, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 629 days.

(21) Appl. No.: 12/534,497

(22) Filed: Aug. 3, 2009

(65) Prior Publication Data

US 2010/0128273 A1 May 27, 2010

(30) Foreign Application Priority Data

Nov. 27, 2008 (KR) .......................... 10-2008-0119075

(51) Int. Cl.
*G01N 21/55* (2014.01)

(52) U.S. Cl.
USPC ........................................................ 356/445

(58) Field of Classification Search
USPC ........................................................ 356/445
See application file for complete search history.

(56) References Cited

U.S. PATENT DOCUMENTS

| | | | | |
|---|---|---|---|---|
| 5,374,563 | A | * 12/1994 | Maule | ............................ 436/165 |
| 2005/0237602 | A1 | * 10/2005 | Yanagisawa | ................... 359/340 |
| 2006/0238767 | A1 | * 10/2006 | Chen et al. | .................... 356/445 |
| 2009/0141376 | A1 | 6/2009 | Smith et al. | |

FOREIGN PATENT DOCUMENTS

| JP | 10-267841 | * 3/1997 | ............. G01N 21/41 |
|---|---|---|---|
| JP | 10-267841 A | 10/1998 | |
| KR | 10-0602492 | 7/2006 | |
| KR | 10-2007 0081557 A | 8/2007 | |

OTHER PUBLICATIONS

Lee, K.S., et al., "Bimetallic Approach to Enhance the Resolution of Waveguide Coupled Surface Plasmon Resonance Sensor," EOS Annual Meeting 2008, Sep. 29, 2008-Oct. 2, 2008, 2 pages, Paris, France.
PCT International Search Report, PCT Application No. PCT/KR2009/006996, Jul. 13, 2010, 3 pages.

* cited by examiner

*Primary Examiner* — Gregory J Toatley
*Assistant Examiner* — Rebecca C Bryant
(74) *Attorney, Agent, or Firm* — Fenwick & West LLP

(57) ABSTRACT

Provided is a surface plasmon resonance sensor including: a part of delivering light by which a signal beam is incident to generate an evanescent field; and a part of exciting surface plasmon for exciting surface plasmons by the generated evanescent field and giving rise to a surface plasmon resonance, wherein a dielectric waveguide layer is inserted between metal layers of the part of exciting surface plasmon, and surface plasmon resonance properties are changed by an object to be analyzed.

16 Claims, 6 Drawing Sheets

HIGH RESOLUTION SURFACE PLASMON RESONANCE SENSOR AND SENSOR SYSTEM THEREOF

CROSS-REFERENCE TO RELATED APPLICATION

This application claims priority to Republic of Korea Patent Application No. 10-2008-0119075, filed on Nov. 27, 2008, and all the benefits accruing therefrom under 35 U.S.C. §119(a), the contents of which in its entirety are herein incorporated by reference.

BACKGROUND

1. Field

This disclosure relates to a biochemical sensor using the surface plasmon resonance phenomena that occur at an interface between a thin metal film and a dielectric, and more particularly, to a high-resolution surface plasmon resonance sensor and a system using the same, capable of narrowing the reflectivity curve due to the surface plasmon resonance, increasing the electric field intensity near the metal surface, thereby enhancing the responsivity to an environmental change, and extending a dynamic range of the sensor.

2. Description of the Related Art

Surface plasmons are charge density waves of free electrons which occur on a surface of a thin metal film with which a dielectric forms an interface and propagate along the interface. Amplitude of their enhanced electric field has maximum at the metal surface and decays exponentially away from the interface in a perpendicular direction. The surface plasmon is generally excited through a coupling of evanescent field generated by a p-polarized light. Since a resonance condition in which surface plasmons are excited depends on a change in a surrounding environment adjacent to the thin metal film surface very sensitively, bio- and gas sensors using this have been extensively studied and developed.

Conventional surface plasmon resonance sensor has a basic configuration consisting of a prism and a single thin metal layer placed on the bottom of the prism. The thin metal layer can be directly deposited on the prism basal plane. Otherwise, the thin metal layer is coated on a transparent substrate optically coupled with the prism by using refractive index matching oil. When a p-polarized laser light is incident onto the metal layer from a side of the prism, the laser light is totally reflected back into the prism above a critical angle of incidence. However, at a specific incident angle higher than the critical angle satisfying a phase matching condition where a component of the incident light wave vector parallel to the prism interface equal to a wave vector of the surface plasmon, the incident light is transferred to the surface plasmon mode propagating along the interface between the thin metal layer and a surrounding medium, and this creates a sharp dip in the reflectance curve.

Since the resonance condition in which the surface plasmons are excited depends on the environment very sensitively, operations of a surface plasmon resonance sensor are performed by measuring a change in the reflectance dip curve in response to a change in the refractive index of the surrounding medium. Depending on experimental means and selection of factors for observing the changes, various measuring methods are available. When a monochromatic laser light is used, methods of measuring a change in the resonance angle at which the surface plasmons are excited, or measuring a change in intensity or phase of the reflected beam in a state where an incident angle is fixed to the initial resonance angle, are possible. When a multi-chromatic light source is used, the environmental change can be measured by monitoring a change in the resonance wavelength for a particular incident angle using a spectrometer.

Novel metals such as gold (Au), silver (Ag), and copper (Cu) can be used for the excitation of surface plasmon. These metals have advantage in that the surface plasmon damping is small and the sharp resonance properties are exhibited since their optical properties are defined by a Drude free electron model in the region of visible to near-infrared wavelengths and the optical absorption loss of metal itself is small. In view of optical properties, Ag is the best. However, there are problems in that Ag has poor thermal, chemical and mechanical stabilities, and inferior biocompatibility. On the other hand, Au has excellent environmental durability and biocompatibility, and therefore has been most commonly used. However, the optical properties are worse than those of Ag.

For early diagnosis of diseases and pathogen infection and rapid analysis of air and environmental pollution, development of a high-resolution sensor capable of detecting small molecules with a molecular weight below hundreds of Daltons and a trace level concentration as low as tens of femtomoles (fM) is necessary. It has been known that the conventional surface plasmon resonance sensor which mainly uses a single Au layer with a thickness of about 50 nm has a limitation in resolution.

The resolution of surface plasmon resonance sensor is improved as the linewidth of the reflectance dip curve decreases and a shift in the resonance angle or wavelength in response to the environmental index change increases. With limited available metals, most of current efforts have been concentrated on decreasing the linewidth of the resonance curve. The approaches can be classified into a method of using laser light of near-infrared wavelength, a method of applying an Au/Ag bimetal layer, a method of using coupling between plasmonic modes such as long range surface plasmon, and the like, through an optical design of multi-layered stack for surface plasmon excitation.

However, since these methods still have problems in stability and resolution, a surface plasmon resonance sensor with further enhanced stability and resolution is required.

SUMMARY

The present disclosure provides a high-resolution surface plasmon resonance sensor capable of decreasing a linewidth of the reflectance dip curve due to the surface plasmon resonance, and increasing the electric field amplitude near the metal film surface, thereby enhancing the responsivity to an environmental change, especially, in a localized region to the metal surface, extending a dynamic range, and simultaneously, enhancing stability of the sensor.

In one aspect, there is provided a surface plasmon resonance sensor including: a part of delivering light for making a signal beam incident to generate an evanescent field; and a part of exciting surface plasmon for exciting a surface plasmon mode by the generated evanescent field and giving rise to surface plasmon resonance, wherein a dielectric layer is inserted between metal layers of the part of exciting surface plasmon, and surface plasmon resonance properties are changed by an object to be analyzed.

In another aspect, there is provided a surface plasmon resonance sensor system including: a light source for providing a signal beam to generate surface plasmons; a surface plasmon resonance sensor of which surface plasmon resonance properties are changed by an object to be analyzed; and a light detecting part for measuring a reflected beam from the surface plasmon sensor, wherein the surface plasmon resonance sensor includes: a part of delivering light by which the signal beam is propagated to form an evanescent field; and a part of exciting surface plasmon for exciting a surface plasmon by the generated evanescent field and giving rise to surface plasmon resonance, wherein a dielectric layer is inserted between the metal layers of the part of exciting surface plasmon, and the light detecting part monitors a change in resonance properties of the surface plasmon resonance sensor and analyzes the object to be analyzed.

When the surface plasmon resonance sensor according to the embodiment of the disclosure is used, there are advantages in that due to a sharp resonance curve and an effect of local electric field enhancement, the resolution of sensor is remarkably improved to detect a small change in refractive index of a surrounding medium, and especially sensitive to a change in a local environment adjacent to a metal layer surface, and the stability of sensor is significantly enhanced as well.

BRIEF DESCRIPTION OF THE DRAWINGS

The above and other aspects, features and advantages of the disclosed exemplary embodiments will be more apparent from the following detailed description taken in conjunction with the accompanying drawings.

DETAILED DESCRIPTION

Figure 1:
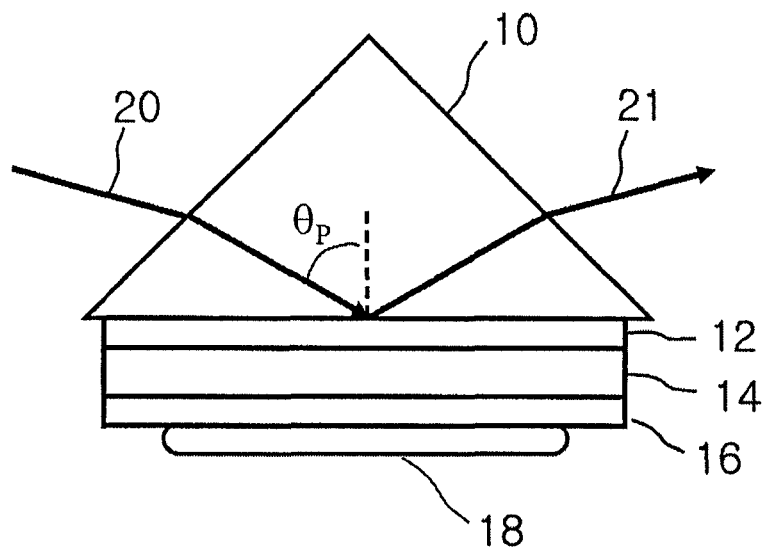
FIG. 1 is a longitudinal sectional view schematically illustrating a surface plasmon resonance sensor according to an embodiment of the disclosure.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

FIG. 1 is a longitudinal sectional view schematically illustrating a surface plasmon resonance sensor according to an embodiment. As illustrated in FIG. 1, the surface plasmon resonance sensor according to the embodiment includes a part of delivering light 10 which generates an evanescent field, and a part of exciting surface plasmon 12, 14, and 16.

In the embodiment illustrated in FIG. 1, the part of delivering light is composed of a prism 10. The part of exciting surface plasmon 12, 14, and 16 is optically coupled to one side of the prism 10. A sequential stack of the inner metal layer 12, the dielectric waveguide layer 14, and the outer metal layer 16 is optically connected to the side of the prism. The inner metal layer 12 is made of silver (Ag) or Ag alloy, and the outer metal layer 16 is made of gold (Au) or Au alloy.

The prism 10 is transparent at the wavelength of operation to enable the p-polarized light 20 incident on a side of the prism 10 to propagate through the prism 10 and totally reflected at the interface between the prism 10 and the part of exciting surface plasmon 12, 14, and 16 generating an evanescent field at the interface. A refractive index of the prism 10 according to the embodiment has to be greater than that of a surrounding medium to be analyzed, and the p-polarized signal beam 20 of visible to near-infrared light is used with a wavelength ranging from 500 to 1800 nm which is lower than interband transition energy of Au.

The p-polarized light 20 incident through the part of delivering light 10 is subjected to total internal reflection at the interface with the part of exciting surface plasmon 12, 14, and 16, and is coupled to a surface plasmon mode on the surface of outer metal layer 16 when a resonance condition is satisfied at a specific angle. As a result, the intensity of reflected light 21 drops at the resonance angle and creates a reflectance dip curve. The optimum condition for the surface plasmon mode coupling sensitively depends on the optical thickness of the dielectric waveguide layer 14, and the deviation from the condition accompanies a surface plasmon damping.

The resonance angle at which the surface plasmon is excited is determined depending on the wavelength of incident light 20, the refractive index of prism 10, the multilayer structure of the part of exciting surface plasmon 12, 14, and 16, the combination of optical constants thereof, and the refractive index of the layer of analyte 18 adjacent to the outer metal layer 16. When the layered structure of the surface plasmon resonance sensor and the wavelength of incident light are determined, the change in the refractive index or thickness of the surrounding analyte 18 gives rise to a shift in the resonance angle, and the operation mechanism of sensor is classified by means of detecting this.

As a material of the dielectric waveguide layer 14, an organic material, an inorganic material, a combination thereof, or a composite thereof may be used without limitations as long as it is optically transparent in the wavelength region of operation. As example of the materials, an inorganic material including oxides such as silicon oxide ($SiO_2$), titanium oxide ($TiO_2$), zirconium oxide ($ZrO_2$), hafnium oxide ($HfO_2$), aluminum oxide ($Al_2O_3$), cadmium oxide (CdO), zinc oxide (ZnO), indium(III) oxide ($In_2O_3$), tin oxide ($SnO_2$), gallium(III) oxide ($Ga_2O_3$), yttrium(III) oxide ($Y_2O_3$), beryllium oxide (BeO), magnesium oxide (MgO), tungsten(III) oxide ($WO_3$), vanadium(III) oxide ($V_2O_3$), barium titanate ($BaTiO_3$), and lead titanate ($PbTiO_3$), nitrides such as silicon nitride ($Si_3N_4$) and aluminum nitride ($Al_3N_4$), phosphides such as indium phosphide (InP) and gallium phosphide (GaP), sulfides such as zinc sulfide (ZnS) and arsenic trisulfide ($As_2S_3$), fluorides such as magnesium fluoride ($MgF_2$), calcium fluoride ($CaF_2$), sodium fluoride (NaF), barium fluoride ($BaF_2$), lead(II) fluoride ($PbF_2$), lithium fluoride (LiF), and lanthanum fluoride (LaF), and a combination thereof, an organic material such as polycarbonate, polymethyl methacrylate (PMMA), polydimethylsiloxane (PDMS), and Teflon, and a combination and a composite thereof can be used.

In addition, a surface plasmon resonance sensor system (not shown) for analyzing an object to be analyzed or an surrounding environment may be implemented by providing a light source which provides a signal beam to the surface plasmon resonance sensor and a light detector which detects the reflected beam from the sensor. The light detector can analyze the object to be analyzed or the surrounding environment by measuring the intensity of the signal beam that is reflected from the sensor.

Figure 2:
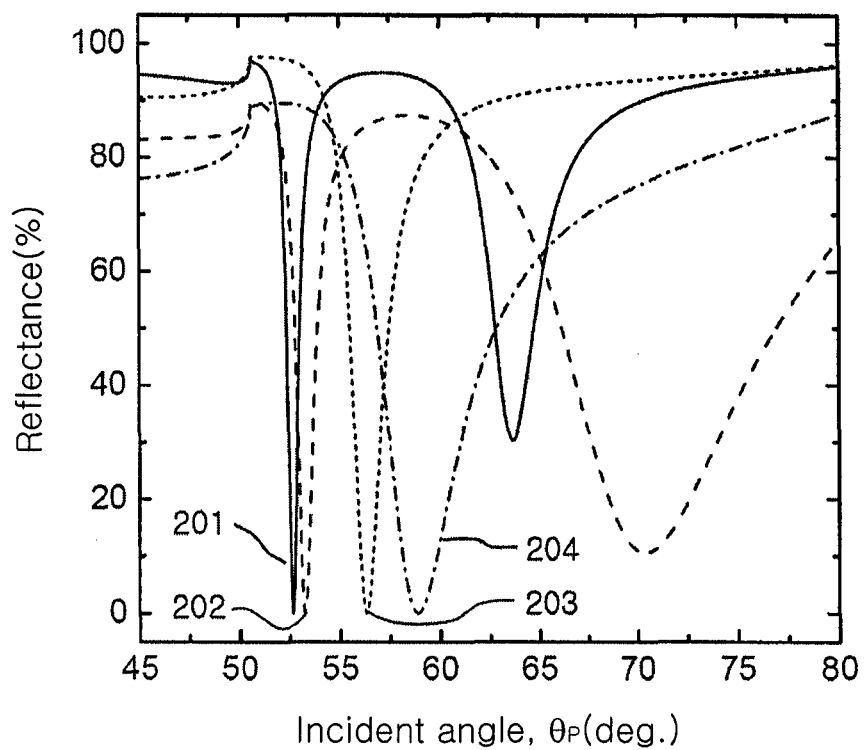
FIG. 2 is a graph showing reflectance curves as a function of incident angle calculated for the surface plasmon resonance sensor according to the embodiment of the disclosure as compared with that of conventional sensor platforms.

FIG. 2 is a graph showing a reflectance curve 201 of the high-resolution surface plasmon resonance sensor according to the embodiment illustrated in FIG. 1, which is theoretically calculated as a function of incident angle $\theta_P$ and compared with that of the conventional sensor configurations 202, 203 and 204. The reflectance of the surface plasmon resonance sensor is measured by the intensity of the reflected signal beam 21 which is totally reflected at the interface between the prism 10 and the part of exciting surface plasmon 12, 14, and 16 and leaves the prism 10.

As an example of the embodiment, the curve 201 of FIG. 2 is obtained by using the SF10 prism 10 and calculating the reflectance of the surface plasmon resonance sensor in which the inner metal layer of Ag 12 with a thickness of 35 nm, the dielectric waveguide layer of $SiO_2$ 14 with a thickness of 370 nm, and the outer metal layer of Au 16 with a thickness of 28 nm are sequentially stacked on the basal plane of the prism 10. It is assumed that the wavelength of incident light is 633 nm and the refractive index of surrounding medium is 1.332, the same as that of water. The results for the conventional sensor configurations are obtained by using the SF10 prism and theoretically calculating the case 204 where a single Au metal layer with a thickness of 50 nm is used for sensing directly formed on the basal plane of the prism, the case 203 where a bimetallic layer consisting of a Ag layer with a thickness of 25 nm and an outer Au layer with a thickness of 20 nm is used, and the case 202 which has a configuration of waveguide-coupled surface plasmon resonance wherein both the outer and inner metal layers 16 and 12 are composed of Au and have respective thicknesses of 28 and 37 nm, and the dielectric waveguide layer of $SiO_2$ 14 with a thickness of 370 nm is inserted between the metal layers to optically couple them.

As illustrated in FIG. 2, the reflectance dip curves arising from the surface plasmon resonance show the narrowest linewidth in the case 201 of using the multilayer stack of Au (28 nm)/$SiO_2$ (370 nm)/Ag (35 nm)/SF10-prism according to the embodiment, and the broadest linewidth in the case 204 of conventional sensor using the Au (50 nm) single layer. Particularly, it is observed that the linewidth of the reflectance dip curve 201 according to the embodiment is significantly narrower than that of the case 203 having the bimetallic layer configuration of Au (20 nm)/Ag (25 nm)/SF10-prism stack with the same thickness ratio of Au to Ag as that of the case 201.

Figure 3:
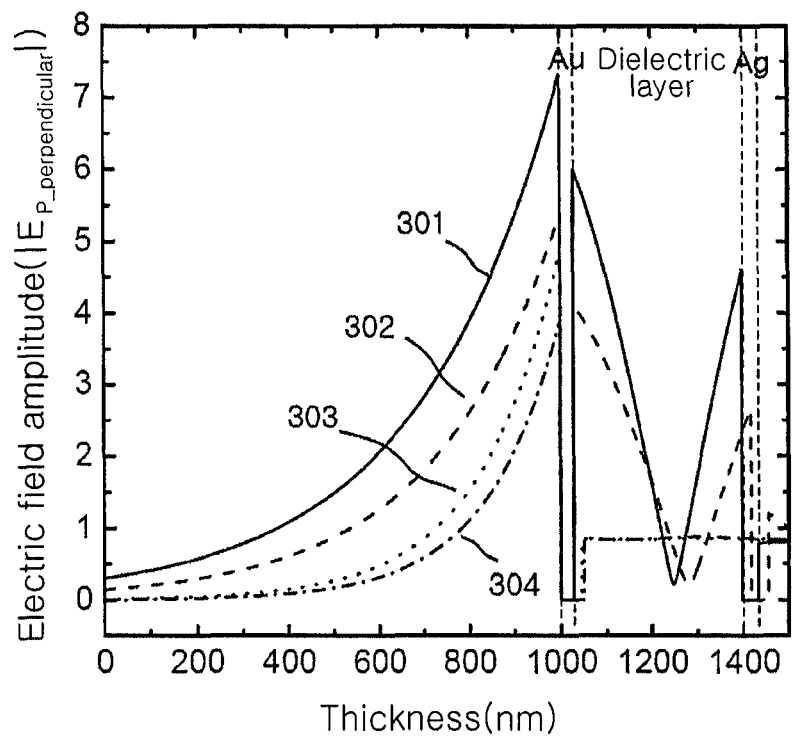
FIG. 3 is a graph showing the electric field distribution of p-polarized light perpendicular to the prism basal plane for the surface plasmon resonance sensor according to the embodiment as compared with that of conventional sensor configurations, which are calculated as a function of thickness extending to the surrounding medium.

FIG. 3 is a graph showing the distribution of perpendicular component of electric field amplitude to the prism base for the surface plasmon resonance sensor according to the embodiment and the conventional sensor configurations compared in FIG. 2, which is theoretically calculated as a function of thickness extending to the surrounding. As deduced from the tendency of linewidth as shown in FIG. 2, it is observed that the case 301 of the Au (28 nm)/$SiO_2$ (370 nm)/Ag (35 nm)/SF10-prism stack according to the embodiment exhibits the largest local field enhancement near the surface of outer metal layer 16 adjacent to the surrounding medium. Especially, comparing with the case 302 of the conventional waveguide-coupled surface plasmon resonance sensor having the multilayer stack of Au (28 nm)/$SiO_2$ (370 nm)/Au (37 nm)/SF10-prism in which both of the outer and the inner metal layers 16 and 12 are composed of the same Au material, it is clear that the amplitude of electric field near the metal surface as well as the sharpness of reflectance dip curve are significantly enhanced.

In the electric field amplitude distribution of the waveguide-coupled surface plasmon resonance sensor of FIG. 3, when the condition for the resonance coupling between the modes of surface plasmon and a guided wave is satisfied, it is shown that the electric field of p-polarized light normal to the prism/multilayer interface forms a node at a center portion of the waveguide and makes peak at the interfaces with the outer and the inner metal layers, but the magnitude thereof is lower than the electric field strength enhanced at the surface of outer metal layer adjacent to the surrounding medium by the resonance coupling.

Figure 4:
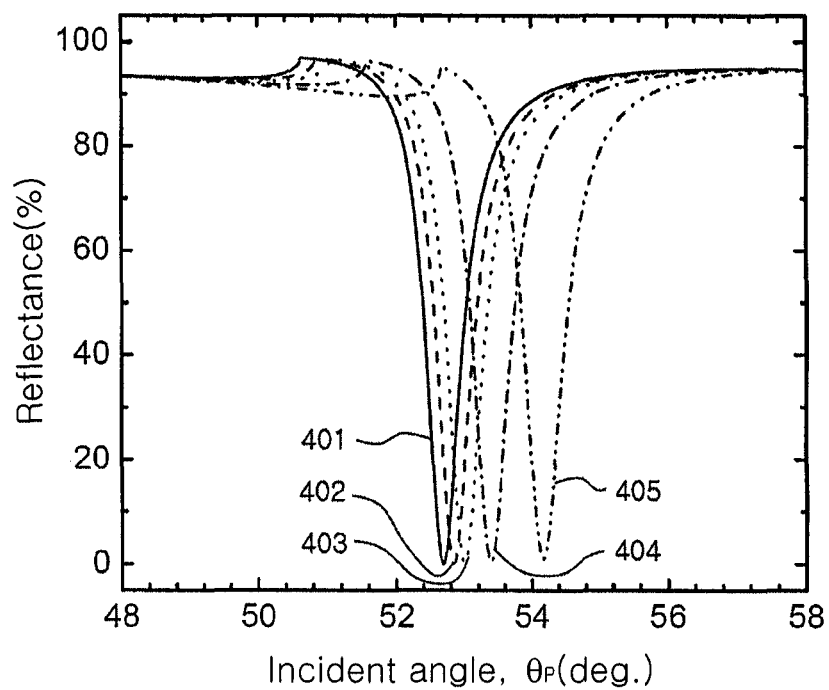
FIG. 4 is a graph showing the reflectance curves of the surface plasmon resonance sensor according to the embodiment as a function of incident angle in response to the change in the bulk refractive index of the surrounding medium.

FIG. 4 is a graph illustrating the reflectance curves 401, 402, 403, 404, and 405 calculated for the surface plasmon resonance sensor having the Au (28 nm)/SiO$_2$ (370 nm)/Ag (35 nm)/SF10-prism stack according to the embodiment which has been changed depending on the bulk refractive index of surrounding medium, that is a refractive index of the analyte layer 18 whose thickness is large enough compared to the decay length of surface plasmon, where the bulk refractive indices of the surrounding medium are assumed to be 1.332 (401), 1.336 (402), 1.340 (403), 1.350 (404), and 1.370 (405). As shown in the graph, the surface plasmon resonance angle, at which the reflectance dip occurs, shifts towards the higher incident angle with increasing the refractive index of the surrounding medium.

Figure 5:
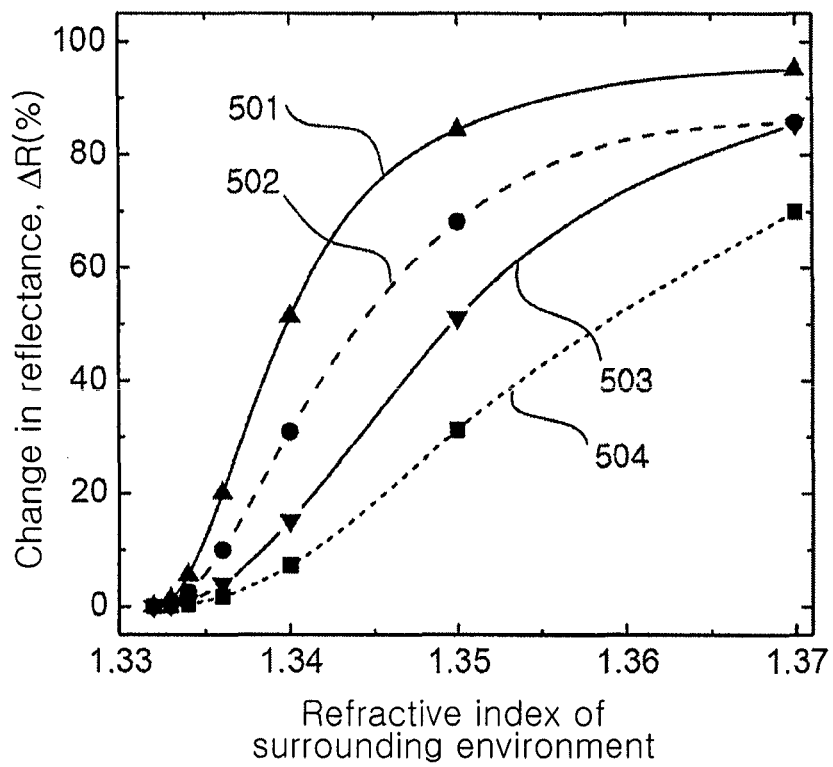
FIG. 5 is a graph showing the reflectance change at the angle of initial resonance calculated for the surface plasmon resonance sensor according to the embodiment in response to the change in the bulk refractive index of the surrounding medium comparing with that of conventional sensor configurations.

FIG. 5 is a graph comparing the reflectance change calculated for the various configurations used in FIG. 2 in response to the change in bulk refractive index of the surrounding medium at the angle of initial resonance when the refractive index of surrounding medium is 1.332. It can be seen that the reflectance change of the Au (28 nm)/SiO$_2$ (370 nm)/Ag (35 nm)/SF10-prism stack 501 according to the embodiment responds to a small change in the refractive index of surrounding medium more sensitively than the other conventional configurations 502, 503, and 504. The curves 502, 503, and 504 represent the response curves of the conventional sensor configurations corresponding to the Au (28 nm)/SiO$_2$ (370 nm)/Au (37 nm)/SF10-prism stack 502, the Au (25 nm)/Ag (20 nm)/SF10-prism stack 503, and the stack of single Au (50 nm) layer on SF10 prism 504, respectively.

Figure 6:
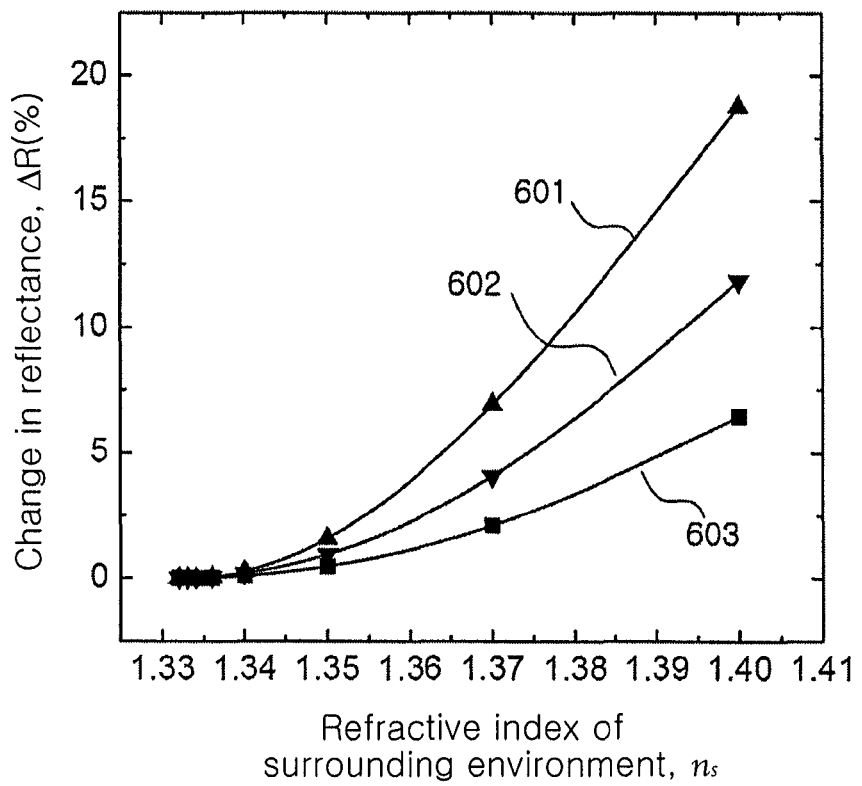
FIG. 6 is a graph showing the reflectance at the angle of initial resonance calculated for the surface plasmon resonance sensor according to the embodiment in response to the refractive index change of thin analytes with a thickness of 10 nm on a metal surface, as compared with that of conventional sensor configurations.

FIG. 6 shows the responses of the sensor configurations represented above in the case where only the 10 nm thick analysis layer 18 on the metal surface changes its refractive index from 1.332 to 1.400 while the bulk refractive index of the surrounding medium is remained at 1.332. Similarly to the case of the bulk index change of whole surrounding medium, the configuration 601 of present invention exhibits the most sensitive response. The curves 602 and 603 corresponds to the results calculated for the Au (20 nm)/Ag (25 nm)/SF10-prism stack 602 using the bimetallic layers and the Au (50 nm)/SF10-prism stack 603 using the single Au layer, respectively. Besides the bulk sensitivity, it is clear that the surface plasmon resonance sensor according to the embodiment exhibits a remarkably improved responsivity to the change in refractive index of the thin analytes adjacent to the metal surface as compared with that of conventional configuration using the simple bimetallic layer with the same thickness ratio of Au/Ag.

The thin analytes of a thickness from a few nanometers to tens of nanometers represent a situation that frequently occurs when the Au metal surface is functionalized with a probe molecule with a specific binding property for a target molecule to be analyzed, in order to enhance the selectivity of a bio-chemical sensor. Examples of types of binding pairs are antigen-antibody, enzyme-substrate, receptor-ligand, protein-DNA, etc.

Figure 7:
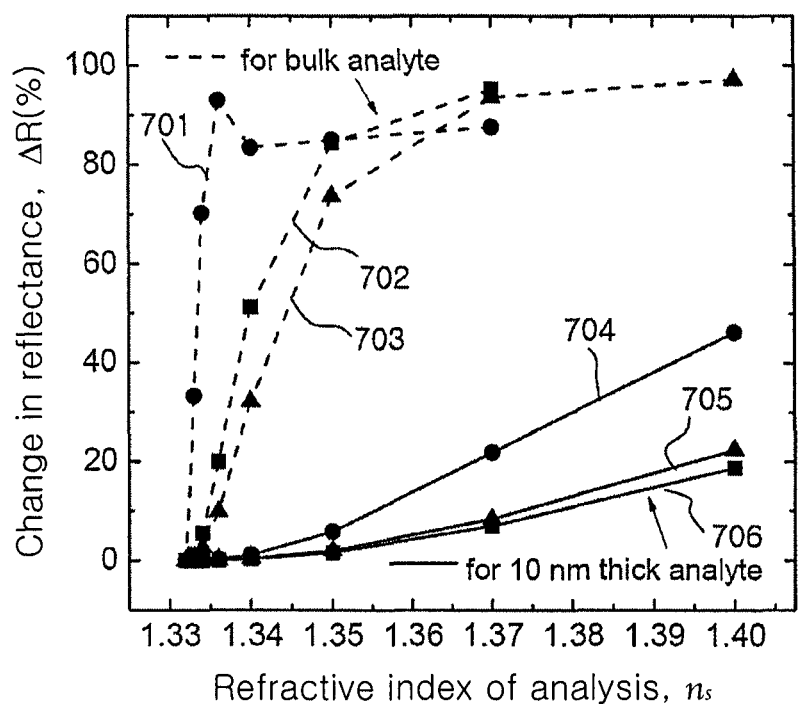
FIG. 7 is a graph showing the dependence of the response to an environmental change on the thickness ratio between a gold (Au) and a silver (Ag) layer of the surface plasmon resonance sensors according to the embodiment.

FIG. 7 is a graph showing that the responsivity to the environmental change can be further enhanced by controlling a thickness ratio between the outer Au layer 16 and the inner Ag layer 12 in the surface plasmon resonance sensor according to the embodiment. Shown are the reflectance changes in response to the change of refractive index in both bulk and thin analytes calculated for the cases 702 and 706 of the Au (28 nm)/SiO$_2$ (370 nm)/Ag (35 nm)/SF10-prism stack which is one of the embodiment illustrated in FIGS. 5 and 6, and for the cases 701 and 704 of the Au (12 nm)/SiO$_2$ (370 nm)/Ag (45 nm)/SF10-prism stack in which the relative ratio of Ag to Au increases to 3.75. The curves 701 and 702 represent the response curves for the refractive index change of the bulk analytes, and the curves 704 and 706 represent the response curves for the analytes with a thickness of 10 nm. As the relative ratio of Ag to Au increases, the linewidth of the reflectance dip curve significantly decreases, and correspondingly the resolution of the sensor is considerably improved to detect the smaller change in the refractive index of surrounding medium.

In FIG. 7, the responses 703 and 705 of the conventional configuration using a bimetallic layer of Au (10 nm)/Ag (36 nm) with the Au/Ag ratio similar to that of the embodiment is also included for comparison. As the ratio of Ag increases, it is observed that the resolution enhancement in the surface plasmon resonance sensor according to the embodiment is getting more significant compared with that of the conventional configuration using simple Au/Ag bimetallic layer.

Figure 8:
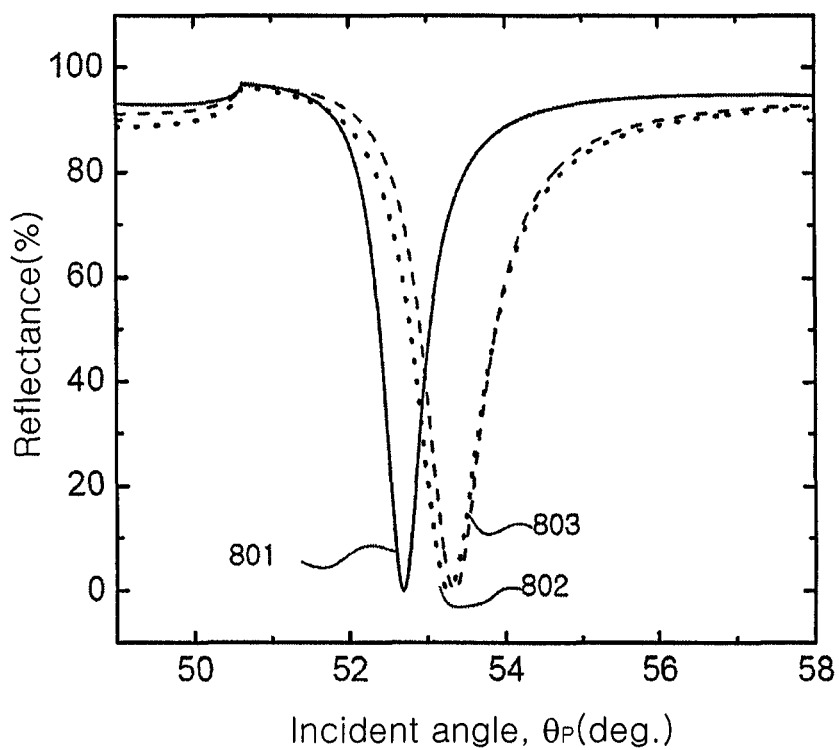
FIG. 8 is a graph showing the effect of materials selection for the dielectric waveguide layer on the reflectance curve as a function of incident angle calculated for the surface plasmon resonance sensor according to the embodiment.

FIG. 8 is a graph illustrating the reflectance dip curves depending on the material selection of the dielectric waveguide layer in the surface plasmon resonance sensor according to the embodiment. With the thicknesses of the outer Au layer and the inner Ag layer fixed to 28 nm and 35 nm, respectively, SiO$_2$, Al$_2$O$_3$, and TiO$_2$ are selected as the dielectric material, and the waveguide thickness of each case is determined to optimize the surface plasmon resonance properties. The optimum thickness of the waveguide layer decreases as the refractive index of the dielectric materials increases. In the cases of using SiO$_2$, Al$_2$O$_3$, and TiO$_2$, the waveguide thicknesses are optimized at 370 nm, 207 nm, and 93 nm, respectively. When the refractive index of dielectric waveguide layer is larger than that of prism like the case of using Al$_2$O$_3$ 803 and TiO$_2$ 802, it can be seen that the reflectance dip curve becomes slightly broader than the case 801 using the low index SiO$_2$, and the angle of resonance increases as well.

Interestingly, however, the trace of reflectance change relative to the change in the refractive index of surrounding medium appears to be almost the same irrespective of the type of dielectric material (not shown). The local electric field strength at the surface of the Au outer metal layer 16 is also observed (not shown) to have a constant distribution regardless of the type of dielectric material. This is apparently different from the case of the conventional long-range surface plasmon resonance sensor, which verifies a great flexibility in selecting the dielectric materials without any limitation in usable range of their refractive index.

Figure 9:
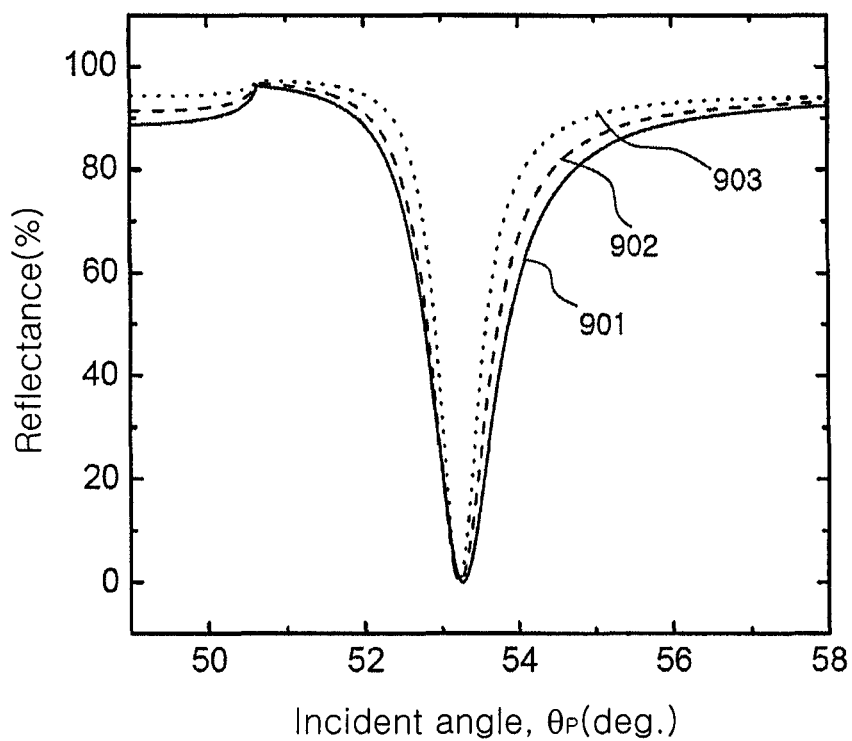
FIG. 9 is a graph showing the effect of resonance thickness of the dielectric waveguide layer on the reflectance curve as a function of incident angle calculated for the surface plasmon resonance sensor according to the embodiment.

FIG. 9 is a graph showing the reflectance dip curves obtained with increasing the waveguide thickness for the stack using TiO$_2$ dielectric waveguide layer in the embodiment of FIG. 8 when the thicknesses are optimized for the surface plasmon resonance. Interestingly, the surface plasmon resonance is optimized at certain periods of waveguide thickness, and as the periodic resonance thickness of dielectric waveguide layer increases, the linewidth of the reflectance curve is gradually decreased without a noticeable change in resonance angle. In the stack of the embodiment, the resonance period of the TiO$_2$ waveguide thickness is estimated to be 135 nm. The curves 901, 902, and 903 of FIG. 9 represent the cases where the thickness of the TiO$_2$ waveguide layer is 93 nm, 362 nm, and 1035 nm, respectively.

Figure 10:
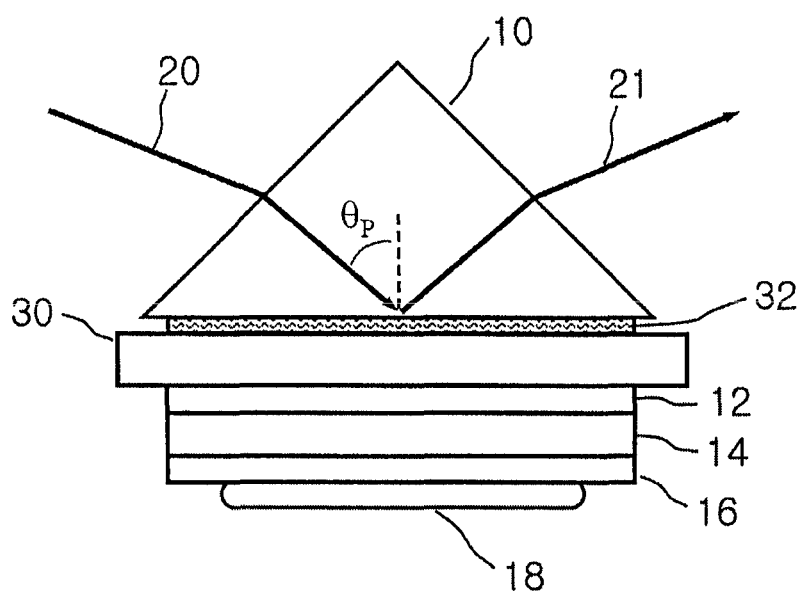
FIG. 10 is a longitudinal sectional view schematically illustrating a surface plasmon resonance sensor according to another embodiment.

FIG. 10 is a longitudinal sectional view schematically illustrating the surface plasmon resonance sensor according to another embodiment. Referring to FIG. 10, the surface plasmon resonance sensor according to this embodiment includes a part of delivering light 10, 30, and 32 which generates an evanescent field and a part of exciting surface plasmon 12, 14, and 16. The part of delivering light includes a prism 10, a refractive index matching oil layer 32, and a transparent substrate 30.

Unlike the embodiment in which the part of exciting surface plasmon 12, 14, and 16 are directly formed on the basal plane of the prism 10, in this another embodiment, a transparent substrate 30 made of a material which is optically transparent in the wavelength of operation such as soda-lime glass, borosilicate glass, and fused silica glass is applied. To the bottom of the transparent substrate 30, the part of exciting surface plasmon 12, 14, and 16 make a sequential stack optically connected, and on the top surface of the transparent substrate 30, the refractive index matching oil layer 32 is disposed. The transparent substrate 30 is optically coupled to the prism 10 by using the refractive index matching oil layer 32. Similarly to the above embodiment, the inner metal layer 12 is made of Ag or Ag alloy, and the outer metal layer is made of Au or Au alloy.

The operation of the surface plasmon resonance sensor according to another embodiment is the same as the surface plasmon resonance sensor according to the above embodiment. However, the use of a film deposition process on the flat substrate 30 instead of direct deposition of the part of exciting surface plasmon 12, 14, and 16 on the prism base 10 has advantages in that the process control for improving film quality and a surface patterning are easy, and since a glass substrate of a relatively lower cost than the prism 10 is used, disposable diagnosis is possible.

However, in the conventional configuration using Au single layer, the refractive index of the transparent substrate 30 needs to be close to that of the prism as much as possible. Thus, the use of a cheaper substrate is limited. Particularly, considering that the use of high refractive index prism somewhat expensive is more advantageous to expand the dynamic range, i.e. the effective range of measurable refractive index by the surface plasmon resonance sensor, it is clear that the benefit of using the low-cost substrate is highly restricted in the conventional sensor using the Au single layer.

Figure 11:
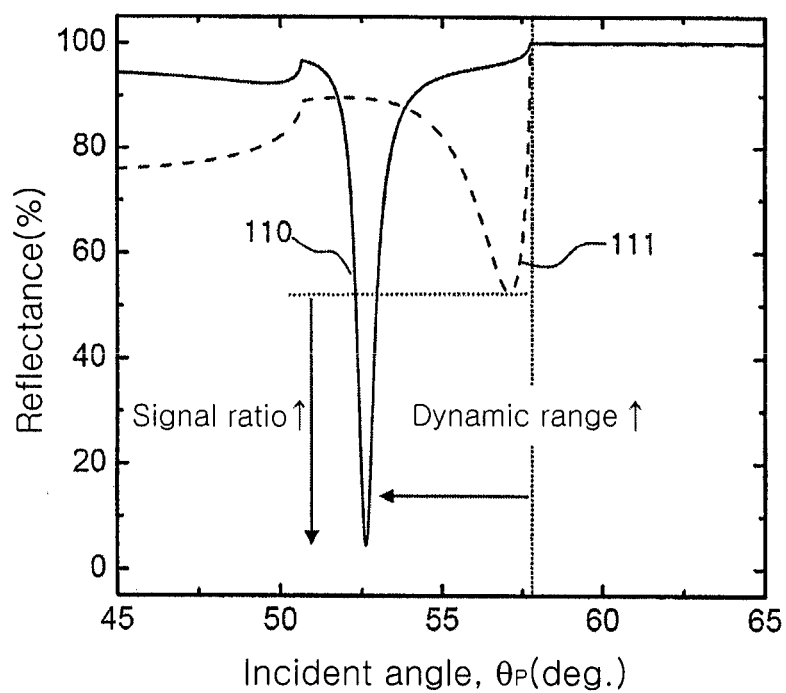
FIG. 11 is a graph showing the reflectance curves as a function of incident angle to demonstrate greater flexibility in selecting a substrate material of the surface plasmon resonance sensor according to the another embodiment, as compared with that of conventional sensor configurations.

In order to explain the advantage of this another embodiment, FIG. 11 shows the reflectance curve for the case where the SF10 prism 10 and the Au (28 nm)/SiO$_2$ (370 nm)/Ag (35 nm) multilayer stack as the part of exciting surface plasmon 12, 14, and 16 are used, as compared with the conventional configuration using the single Au metal layer of a thickness of 50 nm. Here, both cases use the common soda-lime glass of a refractive index of 1.45 as the transparent substrate 30, and the refractive index of the refractive index matching oil layer 32 is assumed to be the same as that of the substrate 30.

As illustrated in FIG. 11, if the refractive index of the substrate is smaller than that of the prism as in the case of the conventional sensor 111, total internal reflection occurs at the interface between the prism 10 and the substrate 30 before the incident light reaches the Au single metal layer on which the surface plasmon is excited, so that the reflectance dip curve become blocked. Even in this situation, the multilayer stack configuration 110 according to this embodiment confirms the wide dynamic range enough for sensor operation due to the enhanced sharpness of reflectance curve and the resonance angle shift to the lower incident angle. In addition, the signal to noise ratio is enhanced by the difference of the reflectance dip levels between both curves 110 and 111.

As the materials of the transparent substrate 30 according to this another embodiment, any organic or inorganic materials can be used without limitations as long as they are optically transparent in the wavelength range of signal beam 20, and the refractive index range thereof is not particularly limited either.

As described above, the surface plasmon resonance sensor according to the embodiment discloses the configuration using the prism to delivery the incident light and generates the evanescent field which is then coupled to the part of exciting surface plasmon. However, this is only an example, and in other embodiments, a configuration using a surface grating as the part of delivering light instead of the prism may be employed to couple the signal beam to the surface of the outer metal layer 16 of the part of exciting surface plasmon.

In addition to the prism 10 whose cross-section in a plane of incidence is triangle, various other types of prism including a cylindrical prism with a hemispherical cross-section, etc may be employed.

Another configuration, in which an additional interfacial layer may be inserted for the enhancement of adhesion between the metal layer, the dielectric waveguide, layer and the prism, is also possible.

As for the method of signal detection, the traditional method is measuring the relative change in reflected intensity at the resonance angle of minimum reflectance. However, performing the sensor operation at such an arbitrary angle position along the reflectance curve, not at the dip position, that the base level of signal reflectance can be maintained to a certain extent in order to improve the signal sensitivity is also possible. Besides, a method of detecting a change in resonance angle in response to a change in refractive index of surrounding medium, a method of detecting a change in resonance wavelength at a fixed specific incident angle using a multi-chromic light source, a method of performing sensor operations by detecting a phase change, and the like may be employed.

In the embodiments, the method of directly observing the change in the surrounding medium to be analyzed is exemplified. However, a sensor operation by adopting an extra sensing layer whose refractive index, volume, or the like is changed very sensitively responding to a target material to be analyzed and detecting the changes induced in the sensing layer may also be used.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. A surface plasmon resonance generator comprising:
   a prism by which an incident light beam is directed to a surface plasmon generator stack for generating an evanescent field at an interface of the prism and the surface plasmon generator stack, the prism having two sides and a base; and
   the surface plasmon generator stack including:
      an inner metal layer having a first surface and a second surface, the first surface in contact with the base of the prism;
      a dielectric waveguide in contact with the second surface of the inner metal layer; and an outer metal layer having a third surface in contact with the dielectric waveguide and a fourth surface adjacent to a surface of an analyte, wherein the surface plasmon generator stack gives rise to propagating surface plasmons of a surface plasmon resonance at the outer metal layer by the evanescent field; and wherein the surface plasmon resonance properties of the surface plasmon generator stack are changed by the analyte disposed on the fourth surface of the outer metal layer, and the responsivity of the plasmon resonance of the surface plasmon generator stack is controlled by controlling a thickness ratio of a first thickness of the inner metal layer to a second thickness of the outer metal layer; and wherein a refractive index of the dielectric waveguide is greater than that of the prism.

2. The surface plasmon resonance generator according to claim 1, wherein:

the inner metal layer is adjacent to the prism and is optically coupled thereto;

the dielectric waveguide is optically coupled to the inner metal layer; and the outer metal layer is optically coupled to the dielectric waveguide, wherein the dielectric waveguide protects the inner metal layer, and increases a control range of the thickness ratio between the inner and outer metal layers.

3. The surface plasmon resonance generator according to claim 1, further comprising an optically reflective interface formed at an interface of the prism and the inner metal layer, the optically reflective interface totally reflecting the incident light beam.

4. The surface plasmon resonance generator according to claim 1, further comprising a light sensor configured to measure a change in the plasmon resonance properties of a light beam reflected by the plasmon generator stack, the light sensor detecting a change of at least one of a resonance angle, a wavelength, a reflected intensity, and a phase of the incident light beam.

5. The surface plasmon resonance generator according to claim 1, wherein the prism includes a surface grating optically coupled to the inner metal layer.

6. The surface plasmon resonance generator according to claim 1, wherein the inner metal layer includes silver (Ag) or an alloy comprising Ag, and the outer metal layer includes gold (Au) or an alloy comprising Au.

7. The surface plasmon resonance generator according to claim 1, wherein the dielectric waveguide is made of a material which is optically transparent in a wavelength region of operation from 500 to 1800 nm.

8. The surface plasmon resonance generator according to claim 1, further comprising:

an optically transparent substrate interposed between the prism and the inner metal layer; and a refractive index matching oil layer interposed between the substrate and the prism to optically couple the substrate and the prism to each other.

9. A surface plasmon resonance sensor system comprising:

a light source for providing a signal beam to generate surface plasmons;

a surface plasmon resonance sensor of which surface plasmon resonance properties are changed by an analyte to be analyzed; and a light detector for measuring a reflected beam which experiences surface plasmon resonance and emerges from the surface plasmon resonance sensor, wherein the surface plasmon resonance sensor includes:

a prism by which the signal beam is propagated to form an evanescent field at an interface of the prism and a surface plasmon generator stack, the prism having a base;

the surface plasmon generator stack including:

an inner metal layer having a first surface and a second surface, the first surface in contact with the base of the prism;

a dielectric waveguide in contact with the second surface of the inner metal layer and an outer metal layer having a third surface in contact with the dielectric waveguide and fourth surface adjacent to a surface of the analyte to be analyzed, wherein the surface plasmon generator stack gives rise to propagating surface plasmons of a surface plasmon resonance at the outer metal layer by the evanescent field, and the surface plasmon resonance properties of the surface plasmon generator stack are changed by the analyte disposed on the fourth surface of the outer metal layer, and the responsivity of the plasmon resonance is controlled by controlling a thickness ratio of a first thickness of the inner metal layer to a second thickness of the outer metal layer; and wherein a refractive index of the dielectric waveguide is greater than that of the prism.

10. The surface plasmon resonance sensor system according to claim 9, wherein the part of exciting surface plasmon includes:

an inner metal layer adjacent to the prism and optically coupled thereto;

the dielectric waveguide optically coupled to the inner metal layer; and the outer metal layer optically coupled to the dielectric waveguide, wherein the dielectric waveguide protects the inner metal layer, and increases a control range of the thickness ratio between the inner and outer metal layers.

11. The surface plasmon resonance sensor system according to claim 10, further comprising a surrounding medium analyte to be analyzed by the surface plasmon resonance sensor system, wherein the surrounding medium analyte is analyzed depending on the surface plasmon resonance properties of the surface plasmon resonance sensor.

12. The surface plasmon resonance sensor system according to claim 10, wherein the surface plasmon resonance sensor is configured to absorb the incident signal beam due to the surface plasmon resonance; and the surface plasmon resonance properties are changed by the analyte to be analyzed and the thickness ratio of the first thickness of the inner metal layer to the second thickness of the outer metal layer.

13. The surface plasmon resonance sensor system according to claim 12, wherein the analyte to be analyzed is analyzed by controlling the surface plasmon resonance properties or the responsivity of the analyte to be analyzed.

14. The surface plasmon resonance sensor system according to claim 10, wherein the change in the surface plasmon resonance properties and the responsivity to the analyte is detectable by measuring a reflectance of the signal beam, and the reflectance is measurable by detecting the intensity of the reflected beam by the light detector.

15. The surface plasmon resonance sensor system according to claim 10, further comprising:

an optically transparent substrate interposed between the prism and the inner metal layer; and a refractive index matching oil layer interposed between the substrate and the prism to optically couple the substrate and the prism to each other.

16. The surface plasmon resonance sensor system according to claim 11, wherein the refractive index of the prism is greater than that of the analyte to be analyzed or the surrounding medium analyte.

* * * * *